(12) United States Patent
Martinez

(10) Patent No.: US 8,993,011 B2
(45) Date of Patent: *Mar. 31, 2015

(54) SWINGLEA GLUTINOSA LEAVES DERIVED MATERIAL IN COMBINATION WITH PYRETHROIDS FOR CONTROL OF ACARI

(75) Inventor: Jamez Alberto Jimenez Martinez, Medellin (CO)

(73) Assignee: Ecoflora Agro SAS, Rionegro, Antioquia (CO)

( * ) Notice: Subject to any disclaimer, the term of this patent is extended or adjusted under 35 U.S.C. 154(b) by 682 days.

This patent is subject to a terminal disclaimer.

(21) Appl. No.: 12/945,873

(22) Filed: Nov. 14, 2010

(65) Prior Publication Data
US 2011/0059195 A1 Mar. 10, 2011

Related U.S. Application Data

(63) Continuation-in-part of application No. 12/466,801, filed on May 15, 2009.

(51) Int. Cl.
*A61K 36/00* (2006.01)
*A61K 36/752* (2006.01)
*A01N 25/00* (2006.01)
*A61K 36/75* (2006.01)

(52) U.S. Cl.
CPC ...................................... *A61K 36/75* (2013.01)
USPC ............................ 424/736; 424/774; 424/405

(58) Field of Classification Search
None
See application file for complete search history.

(56) References Cited

U.S. PATENT DOCUMENTS

| | | | |
|---|---|---|---|
| 5,389,662 A * | 2/1995 | Pap et al. ........................ | 514/383 |
| 5,498,624 A | 3/1996 | McLoughlin et al. | |
| 5,948,805 A | 9/1999 | Geddens et al. | |
| 7,297,349 B2 | 11/2007 | Arimoto et al. | |
| 2002/0031538 A1 | 3/2002 | Scarmoutzos | |
| 2010/0291241 A1 | 11/2010 | Restrepo et al. | |
| 2010/0316751 A1 | 12/2010 | Jimenez Martinez et al. | |
| 2011/0020481 A1 | 1/2011 | Jimenez Martinez | |

FOREIGN PATENT DOCUMENTS

WO  WO 2010/131109 A1  11/2010

OTHER PUBLICATIONS

Alvarez et al. ("Controlling powdery mildew of roses using a plant extract and foliar fertilizers", Phytopathology, (Jun. 2001), vol. 91, No. 6, Supplement, pp. 101-102).*

Alvarez, E., et al., "Controlling powdery mildew of roses using a plant extract and foliar fertilizers," *Phytopathology 91*(6):S101, 2001/APS/MSA/SON Annual Meeting, MSA Abstracts, Salt Lake City, United States.

Braga, P.A.C., et al, "In vitro cytotoxicity activity on several cancer cell lines of acridone alkaloids and *N*-phenylethyl-benzamide derivatives from *Swinglea glutionsa* (Bl.) Merr.," *Natural Product Research 21*(1):47-55. Taylor & Francis, England (2007).

Bueno-Sanchez, J.G. et al., "Evaluación de la actividad antimocribaceriana de algunas plantas aromáticas y medicinales que crecen en Colombia." Instituto Nacional de Salud, Grupo de Micobacteriasl, Bogotá, D.C., Centro Colombian de Investigación en Tuberculosis CCITB, Colombia. Universidad industrial de Santander, Bucaramanga, Centro de Investigación en Biomoléculas, CIBIMOL, CENIVAM2. Colombia. Jul. 23-28, 2008.

Dos Santos, D.A.P., et al., "Antiparasitic Activities of Acridone Alkaloids from *Swinglea glutinosa* (Bl.) Merr.," *J. Braz. Chem. Soc. 20*(4): 644-659, Sociedade Brasileira de Quimica, Brazil (Nov. 2009).

Purcaro, R., et al., "Algicide Constituents from *Swinglea glutinosa*," *J. Agric. Food Chem. 57*:10632-10635, American Chemical Society, United States (Oct. 2009).

Weniger, B., et al., "Antiprotozoal activities of Colombian plants," *Journal of Ethnopharmacology 78*(2-3):193-200, Elsevier Science Ireland, Ltd., Ireland (2001).

Weniger, B., et al., "Bioactive Acridone Alkaloids from *Swinglea glutinosa*," *J. Nat. Prod. 64*(9):1221-1223, American Chemical Society and American Society of Pharmacognosy, United States (published online Sep. 8, 2001).

Final Office Action mailed Jun. 8, 2011, in U.S. Appl. No. 12/860,896, filed Aug. 22, 2010, inventors Jimenez Martinez et al.

Non Final Office Action mailed Nov. 12, 2010, in U.S. Appl. No. 12/860,896, filed Aug. 22, 2010, inventors Jimenez Martinez et al.

Final Office Action mailed Jun. 8, 2011, in U.S. Appl. No. 12/891,841, Sep. 28, 2010, inventor Jimenez Martinez.

Non Final Office Action mailed Dec. 15, 2010, in U.S. Appl. No. 12/891,841. Sep. 28, 2010, inventor Jimenez Martinez.

Non Final Office Action mailed May 20, 2014, in U.S. Appl. No. 12/891,841, Sep. 28, 2010, inventor Jimenez Martinez.

Final Office Action mailed May 31, 2011, in U.S. Appl. No. 12/466,801, filed May 15, 2009, inventors Toro Restrepo et al.

Non Final Office Action mailed Nov. 15, 2010, in U.S. Appl. No. 12/466,801, filed May 15, 2009, inventors Toro Restrepo et al.

Non Final Office Action mailed May 12, 2014, in U.S. Appl. No. 12/466,801, filed May 15, 2009, inventors Toro Restrepo et al.

European Patent Search Report completed Aug. 28, 2013, received Sep. 9, 2013 in European Application No. EP 10 77 4608, European Patent Office, Munich, Germany.

* cited by examiner

*Primary Examiner* — Chris R Tate
*Assistant Examiner* — Deborah Davis
(74) *Attorney, Agent, or Firm* — Sterne, Kessler, Goldstein & Fox P.L.L.C.

(57) ABSTRACT

The invention of the present application provides a natural material derived from *Swinglea glutinosa* leaves that in combination with low doses of pyrethroids, maintains the effect of high doses of pyrethroids over mites. The material derived from *Swinglea glutinosa* leaves, in a preparation with pyrethroids, results in a mix material with the potential to lower the doses of synthetic pyrethroids, eliminating the need to use high doses of synthetic pesticides for acari control.

18 Claims, 2 Drawing Sheets

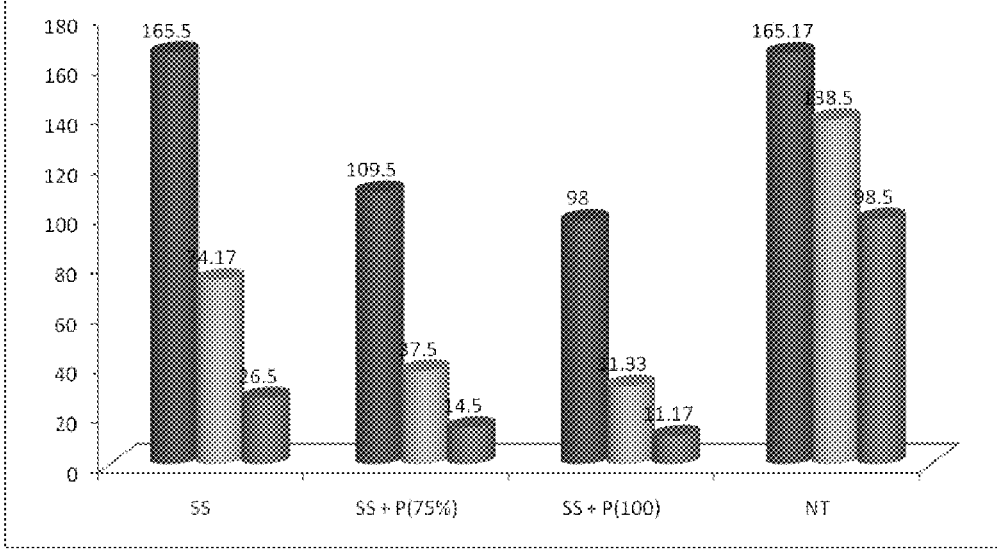
SS = *Swinglea glutinosa* extract 2ml/L
P(75%) = Permethrin 5.6ml/Liter
P(100%) = Permethrin 7.5ml/Liter
NT = no treatment

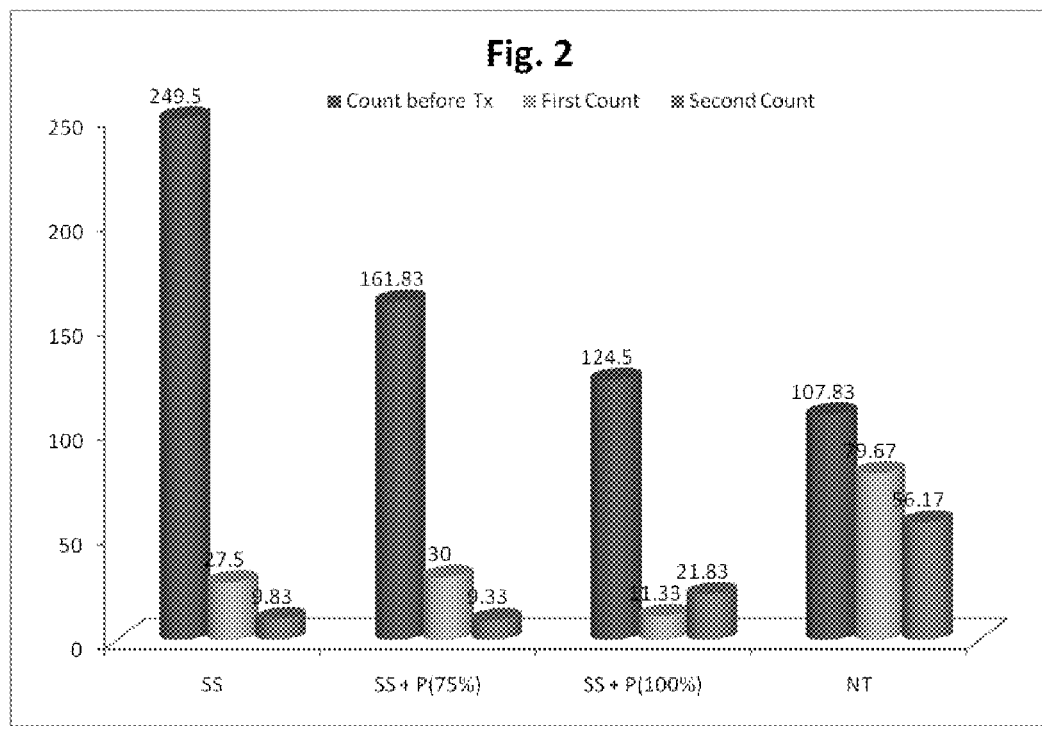
SS = *Swinglea glutinosa* extract 2ml/L
P(75%) = Permethrin 5.6ml/Liter
P(100%) = Permethrin 7.5ml/Liter
NT = no treatment

SWINGLEA GLUTINOSA LEAVES DERIVED MATERIAL IN COMBINATION WITH PYRETHROIDS FOR CONTROL OF ACARI

This application is a continuation in part of U.S. patent application Ser. No. 12/466,801 filed on May 15, 2009, which has one inventor in common. U.S. patent application Ser. No. 12/466,801 is incorporated herein in its entirety by reference.

BACKGROUND OF THE INVENTION

1. Area of the Invention

The present invention is related to how to treat acari with a material derived from *Swinglea glutinosa* leaves and a preparation made of the material derived from *Swinglea glutinosa* leaves and pyrethroids. The material is described by preceding pending unpublished U.S. patent application Ser. No. 12/466,801.

2. Description of Prior Art

Mite pests affect a range of agronomic, vegetable and fruit cultivations causing great losses. Pyrethroids, such as permethrin have been use to control mites. Because, resistance by mites to pyrethroids is common, increasingly high doses of these synthetic pesticide are being used to control these acari. In addition, in order to combat resistance, pyrethroids are used in combination with pesticides, e.g., avermectins.

Unfortunately, the prior art describes few options regarding natural derived compound that can be used in a mix with pyrethroids to diminish resistance by mites to pyrethroids, or to minimize using high doses of synthetic pyrethroids. The Invention of the present application overcomes these prior art limitations.

SUMMARY OF THE INVENTION

The invention of the present application provides a natural material derived from *Swinglea glutinosa* leaves that in combination with low doses of pyrethroids, maintains the effect of high doses of pyrethroids over mites. The material derived from *Swinglea glutinosa* leaves, in a preparation with pyrethroids, results in a mix material with the potential to lower the doses of synthetic pyrethroids, eliminating the need to use high doses of synthetic pesticides for acari control.

More specifically, the invention of the present application provides a preparation that comprises a material derived from *Swinglea glutinosa* leaves and pyrethroids.

In an aspect of the present invention, the preparation is used to treat acari.

In one additional aspect of the present invention, the acari is *Tetranichus* sp.

In another aspect of the present invention, the pyrethroids of the preparation are constituted by permethrin.

In one more aspect of the preparation of the present invention, the material derived from *Swinglea glutinosa* leaves is an extract obtained by a method comprising:
  A. Exposing bright dark green *Swinglea glutinosa* leaves in a dry environment, wherein said leaves are protected from direct sunlight, wherein the leaves are exposed to air flow;
  B. leaving the leaves in the environment described in A. until the leaves turn opaque green and the leaves are brittle;
  C. breaking up the leaves into small fragments;
  D. putting the *Swinglea glutinosa* leaf fragments in contact with a solvent at least once;
  E. repeat step D. until the solvent is enriched with substances derived from the leaf fragments; and,
  F. retiring the solvent to release an extract.

Objectives and advantages of the present application invention will be more evident in the detailed description of the invention and the claims.

BRIEF DESCRIPTION OF THE DRAWINGS

FIG. 1. Shows a graphic of bars illustrating average counts of the amount of *Tetranichus* spp. mobile acari before treatment, three days after the first treatment, and three days after the second treatment.

FIG. 2. Shows a graphic of bars illustrating average counts of the *Tetranichus* spp. eggs before treatment, three days after the first treatment, and three days after the second treatment.

DETAILED DESCRIPTION OF THE INVENTION the invention of the present application provides a preparation that comprises a material derived from *Swinglea glutinosa* leaves and pyrethroids.

In an aspect of the present invention, the preparation is used to treat acari.

In one additional aspect of the present invention, the acari is *Tetranichus* sp.

In another aspect of the present invention, the pyrethroids of the preparation are constituted by permethrin.

In one more aspect of the preparation of the present invention, the material derived from *Swinglea glutinosa* leaves is an extract obtained by a method comprising:
  A. Exposing bright dark green *Swinglea glutinosa* leaves in a dry environment, wherein said leaves are protected from direct sunlight, wherein the leaves are exposed to air flow;
  B. leaving the leaves in the environment described in A. until the leaves turn opaque green and the leaves are brittle;
  C. breaking up the leaves into small fragments;
  D. putting the *Swinglea* glutinosa leaf fragments in contact with a solvent at least once;
  E. repeat step D. until the solvent is enriched with substances derived from the leaf fragments; and,
  F. retiring the solvent to release an extract.

The term acari includes:
*Polyphagotarsonemus* sp.
*Aculops* sp.
*Brevipalpus* sp.
*Aceria* sp.
*Phyllocoptruta* sp.
*Epitrimerus* sp.
*Tetranychus* sp.
*Panonychus* sp.
*Phyllocnistis* sp.
*Scrobipalpula* sp.
*Psylla* sp.
*Boophilus* sp.,
and other species described as acari.

The term acari for purposes of the present invention also covers *Liriomyza* sp. (although technically *Liriomyza* sp. is not an acari), since both the extract from *Swinglea glutinosa* (disclosed in U.S. patent application Ser. No. 12/466,801), and Pyrethroids have been described to kill *Liriomyza* sp.

In one more aspect of the *Swinglea glutinosa* extract of the present invention, in the method, the leaves must not be broken into leaf fragments that are less than 0.5 mm, since smaller fragments would tend to become a single mass which will become a limitation for the optimal extraction with a solvent.

In all cases where a solvent is mentioned in this application, the solvent that can be used comprises ethanol, methanol, hexane, propanol, isopropanol, $CO_2$, acetone, water, ethyl-acetate, nitrile-acetate, toluene, tetrahydrofurane, Chloroform, dichloromethane, and others.

Objectives and advantages of the present application invention will be more evident in the detailed description of the invention and the claims.

EXAMPLES

A test was made by studying four flowered rose plant lots which were infected with *Tetranichus* spp. acari. The number of mobile acari and eggs on leaves of the four flowered rose plant lots were counted one day before treatment. One of four treatments was administered to one four flowered rose plant lot. The four treatments were:

| | |
|---|---|
| 1. *Swinglea glutinosa* | 2 ml/Liter |
| 2. *Swinglea glutinosa* + Permethrin | 2 ml/Liter + 5.6 ml/Liter |
| 3. Permethrin | 7.5 ml/Liter |
| 4. No treatment | |

Each one of the four treatments was administered twice with an interval of seven days between treatments to six infected flowered rose plant lots, respectively. Three days after each treatment the number of mobile acari and eggs were counted again. Each experiment was repeated six times.

Results can be observed in Table 1.

TABLE 1

Mortality of *Tetranichus* sp. Mites

| TREATMENT | Decrease in % mobile acari counted | Decrease in % eggs counted |
|---|---|---|
| SS | 83.9% | 92.05% |
| SS + P (75%) | 86.7% | 94.2% |
| P (100%) | 88.6% | 82.4% |
| NT | 40.3% | 47.9% |

SS = *Swinglea glutinosa* extract 2 ml/L
P (75%) = Permethrin 5.6 ml/Liter
P (100%) = Permethrin 7.5 ml/Liter
NT = no treatment Because of the decrease % for the control (no treatment) a correction on the treatment effect was made by using the Henderson & Tilton formula:

$$\text{Corrected \%} = \left(1 - \frac{n \text{ in } Co \text{ before treatment} * n \text{ in } T \text{ after treatment}}{N \text{ in } Co \text{ after treatment} * n \text{ in } T \text{ before treatment}}\right) * 100$$

Where: n=insect population, T=treated, Co=control

The results show in table 1 show that the combination of a lower dose of permethrin—75%+*Swinglea glutinosa* extract is equivalent to the full dose of permethrin—100%. This result suggest that the use of high doses of permethrin can be lowered by adding *Swinglea glutinosa* extract to permethrin.

FIGS. 1 and 2 show the counts for *Tetranichus* spp. mobile acari and eggs illustrating similar equivalent results for permethrin—75%+*Swinglea glutinosa* extract and permethrin—100%.

The invention claimed is:

1. An acaricide preparation for use in killing acari comprising effective amounts of (i) an extract isolated from *Swinglea glutinosa* leaves and (ii) a synthetic pyrethoid, wherein the *Swinglea glutinosa* extract is obtained by a method comprising contacting *Swinglea glutinosa* leaves with a solvent consisting essentially of a water:organic solvent mixture.

2. The acaricide preparation of claim 1, wherein the acari belongs to the genus *Polyphagotarsonemus, Aculops, Brevipalpus, Aceria, Phyllocoptruta, Epitrimerus, Panonychus, Phyllocnistis,* or *Tetranichus.*

3. The acaricide preparation according to claim 1, wherein the synthetic pyrethroid mix is permethrin.

4. The acaricide preparation according to claim 1, further comprising an avermectin.

5. The acaricide preparation according to claim 1, further comprising camphor, garlic oil, orange oil, lemon oil, lime oil, *Cymbopogon* sp. oil, *Eugenia caryophyllata* oil, *Eucalyptus* sp. oil, *Melaleuca alternifolia* oil, *Citrus sinensis* oil, *Citrus* sp. oil, cinnamon oil, or combinations thereof.

6. A method for the production of an acaricide preparation comprising an extract isolated from *Swinglea glutinosa* leaves and a synthetic pyrethroid, wherein the method comprises:
(a) contacting *Swinglea glutinosa* leaves with a solvent consisting essentially of a water:organic solvent mixture; and,
(b) combining the *Swinglea glutinosa* extract with a synthetic pyrethroid and,
wherein the preparation comprising the *Swinglea glutinosa* extract combined with the synthetic pyrethroid can kill acari.

7. The method according to claim 6, wherein the synthetic pyrethroid is permethrin.

8. The method according to claim 6, further comprising an avermectin.

9. The method according to claim 6, wherein the leaves are leaf fragments.

10. The method according to claim 9, wherein the fragments are larger than 0.05 mm.

11. The method according to claim 6, wherein the organic solvent is water-miscible.

12. The method according to claim 6, wherein the organic solvent is not water-miscible.

13. The method according to claim 6, wherein the organic solvent is selected from the group consisting of ethanol, methanol, hexane, propanol, isopropanol, acetone, ethyl-acetate, nitrile-acetate, toluene, tetrahydrofurane, chloroform, dichloromethane, and combinations thereof.

14. The method according to claim 6, wherein the organic solvent is ethanol.

15. The method according to claim 6, wherein the *Swinglea glutinosa* extract's mass comprises about 60% of the initial leaf mass.

16. The method according to claim 14, wherein the water:ethanol ratio is about 70:320.

17. A method of killing an acari comprising contacting the acari with an effective amount of the acaricide preparation according to claim 1.

18. The method according to claim 17, wherein the acari belongs to the genus *Polyphagotarsonemus, Aculops, Brevipalpus, Aceria, Phyllocoptruta, Epitrimerus, Panonychus, Phyllocnistis,* or *Tetranichus.*

* * * * *